(12) United States Patent
Voegele et al.

(10) Patent No.: US 8,239,007 B2
(45) Date of Patent: Aug. 7, 2012

(54) BIOCOMPATIBLE NANOPARTICLE COMPOSITIONS AND METHODS

(75) Inventors: James W. Voegele, Cincinnati, OH (US); Robert P. Gill, Mason, OH (US); Carl J. Shurtleff, Mason, OH (US)

(73) Assignee: Ethicon Endo-Surgert, Inc., Cincinnati, OH (US)

( * ) Notice: Subject to any disclaimer, the term of this patent is extended or adjusted under 35 U.S.C. 154(b) by 946 days.

(21) Appl. No.: 11/771,384

(22) Filed: Jun. 29, 2007

(65) Prior Publication Data

US 2008/0255537 A1    Oct. 16, 2008

Related U.S. Application Data

(60) Provisional application No. 60/911,546, filed on Apr. 13, 2007.

(51) Int. Cl.
*A61B 1/06* (2006.01)
(52) U.S. Cl. .......................................... 600/476; 424/9.6
(58) Field of Classification Search .................. 424/9.6, 424/9.61, 400, 407, 409, 417, 418; 600/9, 600/11, 12, 407, 473, 476; 604/506, 514
See application file for complete search history.

(56) References Cited

U.S. PATENT DOCUMENTS

| | | |
|---|---|---|
| 4,212,304 A | 7/1980 | Finney |
| 4,264,167 A | 4/1981 | Plummer |
| 4,554,088 A | 11/1985 | Whitehead et al. |
| 4,628,037 A | 12/1986 | Chagnon et al. |
| 4,655,569 A | 4/1987 | Sims |
| 4,672,040 A | 6/1987 | Josephson |
| 4,807,026 A | 2/1989 | Nishioka et al. |
| 4,862,199 A | 8/1989 | Centkowski et al. |
| 5,176,625 A | 1/1993 | Brisson |
| 5,295,954 A | 3/1994 | Sachse |
| 5,406,418 A | 4/1995 | Deary |
| 5,408,996 A | 4/1995 | Salb |
| 5,531,741 A | 7/1996 | Barbacci |
| 5,678,555 A | 10/1997 | O'Connell |
| 5,701,903 A | 12/1997 | Sano et al. |

(Continued)

FOREIGN PATENT DOCUMENTS

DE    102005041271 A1    3/2007

(Continued)

OTHER PUBLICATIONS

Ballou, B. et al., "Sentinel Lymph Node Imaging Using Quantum Dots in Mouse Tumor Models," Bioconjugate Chem., 2007, 18 (2), pp. 389-396.

(Continued)

*Primary Examiner* — Tse Chen
*Assistant Examiner* — Rochelle Reardon (57) ABSTRACT

Various compositions, methods, and devices are provided that use fluorescent nanoparticles, which can function as markers, indicators, and light sources. The fluorescent nanoparticles can be formed from a fluorophore core surrounded by a biocompatible shell, such as a silica shell. In one embodiment, the fluorescent nanoparticles can be delivered to tissue to mark the tissue, enable identification and location of the tissue, and/or illuminate an area surrounding the tissue. In another embodiment, the fluorescent nanoparticles can be used on a device or implant to locate the device or implant in the body, indicate an orientation of the device or implant, and/or illuminate an area surrounding the device or implant. The fluorescent nanoparticles can also be used to provide a therapeutic effect.

13 Claims, 8 Drawing Sheets

U.S. PATENT DOCUMENTS

| | | | |
|---|---|---|---|
| 5,749,830 | A | 5/1998 | Kaneko et al. |
| 5,772,580 | A | 6/1998 | Utsui et al. |
| 5,861,027 | A | 1/1999 | Trapp |
| 5,879,306 | A | 3/1999 | Fontenot et al. |
| 5,954,652 | A | 9/1999 | Heyman |
| 6,013,531 | A | 1/2000 | Wang et al. |
| 6,025,873 | A | 2/2000 | Nishioka et al. |
| 6,028,622 | A | 2/2000 | Suzuki |
| 6,030,339 | A | 2/2000 | Tatsuno et al. |
| 6,044,845 | A | 4/2000 | Lewis |
| 6,069,651 | A | 5/2000 | Tsuyuki et al. |
| 6,110,106 | A | 8/2000 | MacKinnon et al. |
| 6,293,911 | B1 | 9/2001 | Imaizumi et al. |
| 6,310,354 | B1 | 10/2001 | Hanninen et al. |
| 6,344,272 | B1 | 2/2002 | Oldenburg et al. |
| 6,364,855 | B1 | 4/2002 | Zappala |
| 6,395,021 | B1 | 5/2002 | Hart et al. |
| 6,484,049 | B1* | 11/2002 | Seeley et al. ............... 600/426 |
| 6,510,338 | B1 | 1/2003 | Irion et al. |
| 6,530,944 | B2 | 3/2003 | West et al. |
| 6,636,755 | B2 | 10/2003 | Toida |
| 6,773,812 | B2 | 8/2004 | Chandler et al. |
| 7,229,406 | B2 | 6/2007 | Kehr et al. |
| 2002/0029032 | A1 | 3/2002 | Arkin |
| 2002/0115922 | A1 | 8/2002 | Waner et al. |
| 2002/0186921 | A1 | 12/2002 | Schumacher et al. |
| 2003/0060718 | A1 | 3/2003 | Alam et al. |
| 2003/0212324 | A1 | 11/2003 | Knapp et al. |
| 2004/0101822 | A1 | 5/2004 | Wiesner et al. |
| 2004/0190975 | A1 | 9/2004 | Goodman et al. |
| 2004/0225216 | A1 | 11/2004 | Zappala et al. |
| 2004/0241148 | A1 | 12/2004 | Bellomo et al. |
| 2005/0096509 | A1 | 5/2005 | Olson |
| 2005/0182318 | A1 | 8/2005 | Kaji et al. |
| 2005/0191248 | A1 | 9/2005 | Hunter et al. |
| 2005/0192480 | A1 | 9/2005 | Toriya et al. |
| 2005/0277810 | A1 | 12/2005 | Irion |
| 2005/0277963 | A1 | 12/2005 | Fields |
| 2006/0029802 | A1 | 2/2006 | Ying et al. |
| 2006/0089570 | A1 | 4/2006 | Mansour et al. |
| 2006/0159619 | A1 | 7/2006 | Becker et al. |
| 2006/0173362 | A1 | 8/2006 | Toms et al. |
| 2006/0183246 | A1 | 8/2006 | Wiesner et al. |
| 2006/0228554 | A1 | 10/2006 | Tan et al. |
| 2006/0245971 | A1 | 11/2006 | Burns et al. |
| 2007/0016075 | A1 | 1/2007 | Takeda et al. |
| 2007/0059705 | A1 | 3/2007 | Lu et al. |
| 2007/0258908 | A1* | 11/2007 | Lanza et al. ............... 424/9.322 |
| 2007/0260138 | A1* | 11/2007 | Feldman et al. ............ 600/409 |
| 2008/0071208 | A1 | 3/2008 | Voegele et al. |
| 2008/0154102 | A1* | 6/2008 | Frangioni et al. ........... 600/317 |
| 2008/0160090 | A1* | 7/2008 | Oraevsky et al. ........... 424/489 |
| 2008/0213189 | A1 | 9/2008 | Lee et al. |
| 2008/0226562 | A1* | 9/2008 | Groves et al. ............... 424/9.6 |
| 2008/0234566 | A1 | 9/2008 | Voegele et al. |
| 2008/0255403 | A1 | 10/2008 | Voegele et al. |
| 2008/0255414 | A1 | 10/2008 | Voegele et al. |
| 2008/0255425 | A1 | 10/2008 | Voegele et al. |
| 2008/0255459 | A1 | 10/2008 | Voegele et al. |
| 2008/0255460 | A1 | 10/2008 | Voegele et al. |
| 2008/0319307 | A1 | 12/2008 | Voegele et al. |
| 2009/0054761 | A1 | 2/2009 | Voegele et al. |
| 2010/0015607 | A1* | 1/2010 | Geiss et al. ............... 435/6 |

FOREIGN PATENT DOCUMENTS

| | | | |
|---|---|---|---|
| EP | 1310206 | A2 | 5/2003 |
| EP | 1759628 | A1 | 3/2007 |
| JP | 10043205 | A | 2/1998 |
| RU | 2233611 | C2 | 8/2004 |
| WO | WO-02051302 | A2 | 7/2002 |
| WO | WO-2004045649 | A1 | 6/2004 |
| WO | WO-2004108902 | A2 | 12/2004 |
| WO | WO-2006086578 | A1 | 8/2006 |
| WO | WO-2006102307 | A2 | 9/2006 |
| WO | WO-2006110733 | A2 | 10/2006 |
| WO | WO-2007022196 | A2 | 2/2007 |
| WO | WO-2008127880 | A1 | 10/2008 |

OTHER PUBLICATIONS

Partial International Search Report, Annex to Form PCT/ISA/206, PCT/US2008/060045, Mailed Nov. 19, 2009, 10 pages.

Soltesz, E. et al., "Sentinel Lymph Node Mapping of the Gastrointestinal Tract by Using Invisible Light," Annals of Surgical Oncology, vol. 13, No. 3, Mar. 1, 2006, pp. 386-396.

Szentkuti, L., "Light microscopial observations on luminally administered dyes, dextrans, nanospheres and microspheres in the pre-epithelial mucus gel layer of the rat distal colon," Journal of Controlled Release, vol. 46, No. 3, Jun. 2, 1997, pp. 233-242.

Wang, L. et al., "Dual-Luminophore-Doped Silica Nanoparticles for Multiplexed Signaling," Nano Letters, Jan. 2005, vol. 5, No. 1, pp. 37-43.

Yezhelyev, M. et al., "Emerging use of nanoparticles in diagnosis and treatment of breast cancer," Lancet Oncology, Lancet Publishing Group, vol. 7, No. 8, Aug. 2006, pp. 657-667.

"Quantum Dots Could Guide Surgeons", NIBIB, Feb. 11, 2004.

International Search Report mailed Sep. 14, 2010 for App. No. PCT/US2008/060045 (16 pages).

Lu, C. et al., "Bifunctional magnetic silica nanoparticles for highly efficient human stem cell labeling," Nano Letters, Jan. 2007, vol. 7, No. 1, p. 149-154.

Yi, D. K. et al., "Silica-coated Nanocomposites of magnetic nanoparticles and quantum dots," Journal of the American Chemical Society 20050413 US, vol. 127, No. 14, Apr. 13, 2005, p. 4990-4991.

Levy, L. et al., "Nanochemistry: synthesis and characterization of multifunctional nanoclinics for biological application," 2002 Chem. Mater. 14: 3715-3721.

Wang, L. et al., "Multicolor FRET silica nanoparticles by single wavelength excitation," 2006 Nano Lett. 6: 84-88, Epub Dec. 20, 2005.

Xu, C. et al., "Dopamine as a robust anchor to immobilize functional molecules on the iron oxide shell of magnetic nanoparticles," 2004 J. Am. Chem. Soc. 126: 9938-9939.

Rokkanen PU, "Absorbable materials in orthopaedic surgery," 1991 Ann. Med. 23: 109-115.

Troy et al., "Quantitative comparison of the sensitivity of detection of fluorescent and bioluminescent reporters in animal models," 2004 Mol. Imaging 3: 9-23.

* cited by examiner

BIOCOMPATIBLE NANOPARTICLE COMPOSITIONS AND METHODS

CROSS REFERENCE TO RELATED APPLICATIONS

This application claims priority to U.S. Provisional Patent Application No. 60/911,546 filed on Apr. 13, 2007 and entitled "Fluorescent Nanoparticle Compositions, Methods, and Devices," which is hereby incorporated by reference in its entirety.

FIELD OF THE INVENTION

The present invention relates to fluorescent nanoparticles, and in particular to various compositions, methods, and devices that use fluorescent nanoparticles.

BACKGROUND OF THE INVENTION

Illuminating light incident on tissue is transmitted through, scattered by, absorbed, or reflected by that tissue. At certain wavelengths, after absorbing the illuminating light, tissue can re-emit light energy at a different wavelength (autofluorescence). If a substance is introduced into the tissue or is present between tissue layers, or in lumens, it can fluoresce after absorbing incident light as well. Detecting devices can be placed in relationship to the tissue to image light that is transmitted, scattered, reflected, or fluoresced from the tissue. It is well known in the art that certain wavelengths of light tend to be preferentially absorbed, reflected, or transmitted through different types of tissue. Generally, near infrared light (600-1300 nm) tends to coincide with minima in the spectral absorption curve of tissue, and thus allows the deepest penetration and transmission of light. For optical analysis of surface structures or diagnosis of diseases very close to the body surface or body cavity surfaces or lumens, UV light and visible light below 600 nm can also be used, as it tends to be absorbed or reflected near the surface of the tissue.

Various modalities are currently used for imaging of tissue and organs, including visible light endoscopes, ultrasound, magnetic resonance imaging (MRI), computed tomography (CT), and positron emission tomography (PET). Many anatomical spaces and tissues, however, are not easily accessible and viewable. Moreover, the use of imaging equipment can be expensive and time consuming, and their application is often limited.

Various contrast agents are also employed to effect image enhancement in a variety of fields of diagnostic imaging, the most important of these being X-ray, magnetic resonance imaging (MRI), ultrasound imaging, and nuclear medicine. Additionally, optical labels, such as fluorescent dyes, are introduced into tissue samples to signal abnormal biological and/or chemical conditions of tissues of a living subject. Despite many successful applications, conventional optical labels have many drawbacks. For example, conventional optical labels are generally toxic to living cells and tissues comprised of living cells. Additionally, conventional optical labels such as fluorescent dyes generally suffer from short-lived fluorescence because the dyes undergo photo bleaching after minutes of exposure to an excitation light source. This renders them unsuitable for optical imaging that requires extended time period of monitoring. Moreover, conventional optical labels are sensitive to environmental changes such as pH and oxygen concentration. Another drawback of conventional optical labels is that typically the excitation spectra of such labels are quite narrow, while the emission spectra of such labels is relatively broad, resulting in overlapping emission spectra. Thus, when a combination of conventional optical labels with different emission spectra are used in optical imaging, multiple filters are need to detect the resultant emission spectra of the combination. Additionally, fluorescent labels are generally inefficient at converting the excitation light to the emission wavelength, and the resulting signal can be very weak.

Accordingly, there remains a need for improved compositions, methods, and devices for use in medical imagining, and more particularly for marking, indicating, and illuminating tissue.

SUMMARY OF THE INVENTION

The present invention generally provides various compositions, methods, and devices for using fluorescent nanoparticles as markers, indicators, and/or light sources. In one embodiment, an endoscopic adaptor for viewing fluorescent nanoparticles is provided and includes first and second members removably matable to one another, e.g., using threads or other mating elements, and adapted to engage a portion of an endoscope eyepiece therebetween. The first member can have a viewing lumen formed therethrough and adapted to axially align with a viewing lumen formed in an endoscope eyepiece, and a cavity formed therein for seating a filter adapted to filter light received through the viewing lumen of the first member. The device can also include a filter disposed within the cavity in the first member. In an exemplary embodiment, the filter is adapted to transmit light in the fluorescent waveband. For example, the filter can be an interferometric long-pass filter.

The components of the adaptor can have a variety of configurations. In one embodiment, the second member can be in the form of a ring having a lumen extending therethrough with an enlarged diameter portion adapted to receive an enlarged diameter portion formed on an endoscopic eyepiece. The second member can also optionally include first and second hemi-cylindrical halves that are hingedly mated to one another to allow the second member to be positioned around an endoscopic eyepiece. In an another embodiment, the device can include a filter cartridge removably disposed within the first member and adapted to retain a filter therein. For example, the first member can include a slot formed therein and extending across the viewing lumen for receiving the filter cartridge such that a filter containing in the filter cartridge is disposed across the viewing lumen.

In yet another embodiment, an endoscopic system is provided and includes an endoscope eyepiece having a viewing lumen formed therethrough between proximal and distal ends thereof, and an adaptor adapted to removably mate to the endoscope eyepiece and adapted to retain a filter therein such that the filter is in alignment with the viewing lumen formed in the endoscope eyepiece to thereby filter light through the viewing lumen. The adaptor can include a viewing lumen extending therethrough and adapted to be aligned with the viewing lumen in the endoscope eyepiece when the adaptor is mated to the endoscope eyepiece. In an exemplary embodiment, the adaptor can be an eyepiece extension member having the viewing lumen formed therein, and a mating element adapted to mate to the eyepiece extension to engage a portion of the endoscope eyepiece therebetween. A filter can optionally be removably or fixedly disposed within the adaptor. In an exemplary embodiment, the filter is adapted to transmit light in the fluorescent waveband. In other aspects the adaptor can include a filter cartridge removably disposed therein and adapted to retain a filter therein.

Exemplary methods for viewing fluorescent nanoparticles are also provided, and in one embodiment the method can include coupling an adaptor to a proximal end of an endoscope, inserting a distal end of the endoscope into a body lumen to position the distal end in the direction of tissue containing at least one fluorescent nanoparticle, and activating a light transmitting element to emit fluorescent light onto the at least one fluorescent nanoparticle such that reflected fluorescent light is transmitted through a filter contained within the adaptor and is received by an image obtaining element coupled to the endoscope. The light transmitting element can extend through the endoscope to emit fluorescent light onto the at least one fluorescent nanoparticle, and the filter can be configured to block visible light.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1:
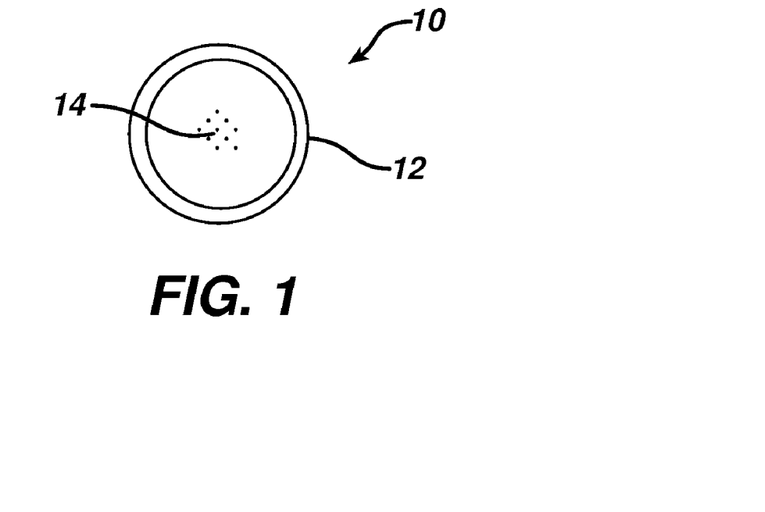
FIG. 1 is a side view of one embodiment of a fluorescent nanoparticle having a core and a shell.

The present invention generally provides various compositions, methods, and devices for using fluorescent nanoparticles in various medical applications. In certain exemplary embodiment, the fluorescent nanoparticles can be used to mark, indicate, and/or illuminate an object, such as a device or tissue. The particular configuration of the fluorescent nanoparticles can vary, but preferably the nanoparticles are biocompatible and non-toxic. The shape, size, and morphology of the nanoparticles can vary. In an exemplary embodiment, as shown in FIG. 1, the nanoparticles 10 can be formed from a fluorophore core 14 and a biocompatible shell 12 that surrounds the core 14. The use of a biocompatible shell is particularly advantageous as it is non-toxic when used in medical applications. The shell can also be configured to intensify the photophysical properties of the core such that, when this dye is excited by light, the observed fluorescence is brighter than the dye itself. This enables viewing through tissue having a thickness of about 2 cm or less.

The particular materials used to form the core and the shell can vary depending on the intended use, but in an exemplary embodiment the core includes organic dye molecules and the shell is silica-based. Fluorescing dyes are available at various wavelengths, including both visible and non-visible wavelengths. Dyes having any wavelength can be used with the present invention, but the particular dye selected may depend on the intended use. For example, where the dye needs to be viewed through tissue, the dye preferably has a wavelength that is near or within the infrared range, i.e., from about 600 nm to 1350 nm. Particular dyes in the near infrared wavelength are preferred as they demonstrate the best transmissibility for passing through tissue. In an exemplary embodiment, the nanoparticles contain a dye that has an absorption and emission cross-section in the region of about 800 nm. Exemplary dyes are Cy 5.5 manufactured by GE Healthcare and Indocyanine Green manufactured by Acros Organics N.V. In order to view dyes with an emission cross-section outside of the visible spectrum for medical applications, energy must be delivered to the dye to excite the molecules and the resulting emission by the molecules must be collected by specialized equipment sensitive to this non-visible waveband. Various exemplary methods and devices for delivering energy to dyes with emission cross-sections outside of the visible spectrum will be discussed in more detail below. Where the dye does not need to be viewed through tissue, or is viewed through very thin tissue, the dye can have a wavelength that is within the visible range, i.e., from about 400 nm to 700 nm. When used in the body, light may need to be delivered to the tissue containing the particles to enable viewing. The light source may be external to the body for delivering light internally, or an internal light source may be used for internal application.

A person skilled in the art will appreciate the fluorescent nanoparticles can be formed from a variety of materials using various methods. Exemplary fluorescent nanoparticles and methods for making the same are disclosed in detail in U.S.

Publication No. 2004/0101822 of Wiesner et al. entitled "Fluorescent Silica-Based Nanoparticles," U.S. Publication No. 2006/0183246 of Wiesner et al. entitled "Fluorescent Silica-Based Nanoparticles," and U.S. Publication No. 2006/0245971 of Burns et al. entitled "Photoluminescent Silica-Based Sensors and Methods of Use," which are hereby incorporated by reference in their entireties. A person skilled in the art will also appreciate that fluorescent semiconductor nanocrystals, also referred to as quantum dots, can also be used with the various methods and devices disclosed herein.

As indicated above, the present invention provides various compositions, methods, and devices that use fluorescent nanoparticles. In one embodiment, fluorescent nanoparticles can be used to locate, mark, or illuminate tissue. For example, one or more nanoparticles can be delivered into or onto tissue, including various body cavities. The nanoparticle(s) can illuminate an area surrounding the tissue when energy is delivered thereto, or they can enable the tissue containing the particles to be located. The nanoparticles can also be used to mark the tissue, thus enabling future identification and location of the tissue. A person skilled in the art will appreciate that the particular tissue or body lumen to be located, marked, or illuminated, as well as the technique for delivering the nanoparticles to the tissue, can vary and the following techniques are merely exemplary.

In one embodiment the nanoparticles can be used to locate a structure that traverses through other tissue or is otherwise visually inaccessible. Many tubular structures, such as the ureter, are not completely visually accessible, but rather traverse through other tissue and thus are difficult to locate and/or view. Various regions of the colon can also be difficult at times to access visually. A solution containing one or more fluorescent nanoparticles can thus be delivered to the structure of interest to enable a surgeon to locate the structure. The method of delivery can vary. For example, the fluorescent nanoparticles can be disposed in a liquid, foam, or gel solution, such as a saline solution, and they can be delivered, for example, using an intravenous (IV) drip or by direct injection into the tissue. Where the solution has a low viscosity, the structure can be isolated, e.g., clamped off or otherwise closed, to contain a finite volume of particles therein, or an open line, such as a saline drip, can be continuously fed to the structure. Alternatively, the solution can be modified to have a high viscosity and/or to contain adhesives. Exemplary solutions will be discussed in more detail below. Once the solutions is delivered to the structure, energy can be applied to the area to excite the nanoparticle(s), thereby enabling the precise location of the particle(s), and thus the structure containing the particle(s), to be determined.

In yet another embodiment, the nanoparticles can have a property that enables them to be filtered into a desired structure, such as the ureter or colon. In particular, delivery to the kidney will enable filtration into the ureter, and delivery to the liver will enable filtration into the colon. For delivery to the ureter via the kidney, the particles typically have a size in the range of about 4 nm to 11 nm, whereas the particles typically have a size that is greater than about 12 nm for delivery to the colon via the liver. Various delivery techniques can be used, including those previously discussed, such as IV delivery into the patient's circulatory system. Once delivered into the body and filtered into the structure to be located, e.g., the ureter or colon, energy can be delivered to the vicinity to excite the particle(s), thereby enabling the precise location of the particle(s), and thus the structure containing the particle(s), to be determined.

In yet another embodiment, the nanoparticles can be used to identify the spread of cancerous cells. With certain types of cancer, such as breast cancer, the nanoparticles can be injected into the tumor. The nanoparticles will be carried into other parts of the body by way of the blood or lymphatic vessels or membranous surfaces. Energy can thus be delivered to the body to locate the nanoparticles and thereby identify whether the tumor has spread. This is particularly useful in determining whether cancerous cells have reached the sentinel lymph node. The use of nanoparticles formed from a fluorophore center core and a biocompatible shell is also advantageous as it provides a non-toxic method for locating cancerous cells, unlike prior art methods which utilize radio-isotopes and semi-conductive nanoparticles which contain toxic metals.

A person skilled in the art will appreciate that the aforementioned techniques can be used to locate any structure. By way of non-limiting example, other exemplary structures include the structures in the biliary system, the lymphatic system, and the circulatory system.

The present invention also provides methods for marking tissue. In one embodiment, the nanoparticles, or a solution containing one or more nanoparticles, can be applied or "painted" onto a tissue surface, or injected into tissue. The applied nanoparticles can function as a marking used to allow for subsequent identification of the tissue. For example, during a colonoscopy the nanoparticles can be applied to or near a polyp that cannot be removed during the procedure. During a subsequent procedure, the nanoparticles can be excited with energy and used to locate and identify the polyp, for example from the abdominal perspective. The markings can also be used to indicate orientation. For example, directional markings, such as arrows or other lines, can be made with the nanoparticles. Various applicators, such as a paint brush or similar applicator, can be used, and an exemplary applicator will be discussed in more detail below. In another embodiment, the markings can be used to detect leaks, for example in a closed system fluid based implant, such as with gastric bands. One failure mode experienced with gastric band is that the system can leak due to punctures of the catheter with a needle during an adjustment, undetected puncturing of the balloon with a suture needle during surgery, and partially or completely disconnected catheter-to-port connections. The fluorescent nanoparticles can be delivered to the band, e.g., in a solution, and their disappearance from the band system or their location outside of the band system in the body can be used to indicate the presence of a leak.

In another embodiment, fluorescent nanoparticles can be used to illuminate tissue. For example, the nanoparticles can be applied to a tissue surface in a body cavity to illuminate the body cavity, such as the stomach, uterus, abdominal cavity, thoracic cavity, vaginal canal, nasal passages, and ear canal. By way of non-limiting example, the nanoparticles can be disposed within a gel, such as KY® Jelly, carboxy methyl cellulose, collagen, or hydrogel, and delivered to the uterus by brushing or otherwise applying the particles to an inner surface of the uterus. Upon energy delivery, the nanoparticles are effective to illuminate the uterus, thereby facilitating viewing during a hysterectomy or other procedures. Similarly, the nanoparticles can be applied to an area of tissue within the stomach to thereby illuminate the stomach during various procedures. A person skilled in the art will appreciate that the nanoparticles can be used to illuminate virtually any body cavity.

Figure 2:
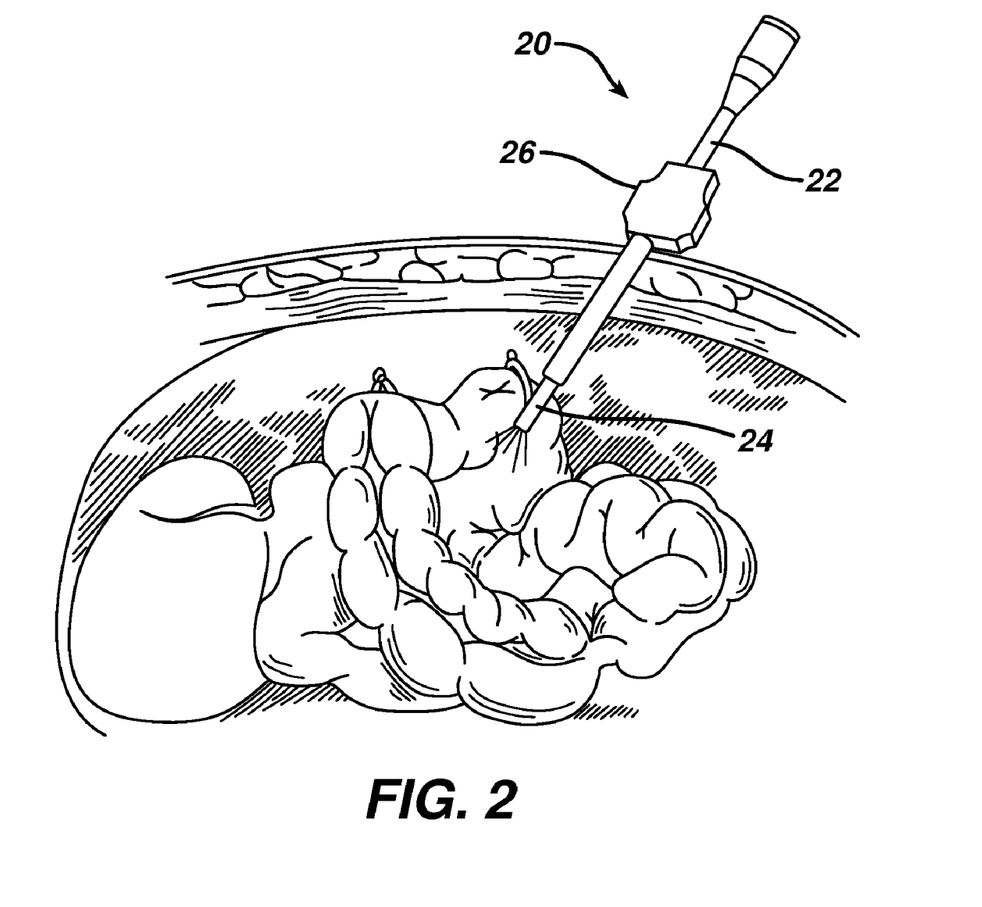
FIG. 2 is a perspective view of one embodiment of an applicator for applying fluorescent nanoparticles to a tissue surface.

As indicated above, various devices can be used to apply the particles to a tissue surface, including rigid and flexible devices, such as elongate shafts, syringes, or hand held pens with marking tips configured to coat, inject, or otherwise deliver the nanoparticles to tissue. The markings can also be applied manually using ones finger tips. FIG. 2 illustrates one exemplary embodiment of a marking device 20. As shown, the marking device 20 has an elongate shaft 22 with a distal tip 24. The elongate shaft 22 can have a variety of configurations, and the particular configuration can vary depending on the mode of insertion. In the illustrated embodiment, the elongate shaft 22 is disposed through a cannula having a working channel that extends into a body cavity. The elongate shaft 22 can also include one or more lumens formed therein and extending between proximal and distal ends thereof. The lumens can be used to deliver a nanoparticle solution to the distal tip 24. The distal tip 24 can also have a variety of configurations. In the illustrated embodiment, the distal tip 24 has a nozzle formed thereon for spraying the nanoparticles onto a tissue surface. In other embodiments, the tip 24 can include a brush for brushing the particles onto a tissue surface. Again, the particular configuration can vary depending on the intended use.

In use, as indicated above, the marking device 20 can be inserted through the trocar 26 that extends through a tissue surface and into the abdominal cavity. Endoscopes or other access devices can also optionally be used, and/or the device can be introduced through a natural orifice or through a man-made orifice. Once positioned adjacent to a target tissue, the marking device 20 can be manipulated using, for example, controls to articulate the distal end of the device and controls to actuate the nozzle, to apply the nanoparticles to the tissue surface. A person skilled in the art will appreciate that a variety of marking devices known in the art can be used. By way of non-limiting example, U.S. patent application Ser. No. 11/533,506 of Voegele de et al., filed on Sep. 20, 2006 and entitled "Dispensing Fingertip Surgical Instrument," which is incorporated herein by reference in its entirety, discloses one exemplary embodiment of a marking device that can be used to apply nanoparticles to a tissue surface.

In each of the various embodiments disclosed herein the nanoparticles can optionally be delivered in a carrier. The particular composition of the carrier can vary, and suitable carriers include any biocompatible liquid, foam, gel, or solid. The carrier and/or the nanoparticles can also include other substances, such as pharmaceutical and/or therapeutic substances. In one exemplary embodiment a more viscous liquid, foam, or gel is used to prevent or delay the particles from being flushed from the tissue site. Exemplary high viscosity liquids include, by way of non-limiting example, KY® Jelly, carboxy methyl cellulose, collagen, and hydrogel. The solution can also optionally have adhesive properties to help retain the nanoparticles in a desired location. Exemplary adhesives are disclosed, by way of non-limiting example, in U.S. Publication No. 2004/0190975 of Goodman entitled "Applicators, Dispensers and Methods for Dispensing and Applying Adhesive Material," which is hereby incorporated by reference in its entirety. This reference also discloses various exemplary applicator devices that can be used to deliver nanoparticles to tissue. The nanoparticles can also be combined with existing marking fluids, such as biocompatible dyes, stains, or colored adhesives. A person skilled in the art will appreciate that any carrier can be used.

The composition of the fluorescent nanoparticles can also vary to provide different functions. In one embodiment, a combination of visible and non-visible dyes can be used to form fluorescent nanoparticles for use in marking tissue. Such dual- or multi-wavelength nanoparticles can be delivered to tissue and, once delivered, the visible dyes can be used to quickly locate a tissue containing the particles and the non-visible dyes can provide more precise viewing. By way of non-limiting example, nanoparticles containing visible and non-visible dyes can be delivered to the ureter. Visible dyes located near the surface can be viewed with visible light to help locate the ureter. Once located, an infrared light can be used to see the non-visible dye locating the ureter path located deeper within tissue. Exemplary viewing methods will be discussed in more detail below. While visible fluorescent dyes are preferred, other types of visible dyes may be used in combination with non-visible fluorescent nanoparticles.

In other embodiments, the composition can be adapted to provide a therapeutic effect. For example, a magnetic material can be used with the fluorescent nanoparticles to enable therapeutic energy to be delivered to tissue. Various techniques can be used to associate a magnetic material with the nanoparticles. For example, the particles can be manufactured with a magnetic or magnetic-containing core. Alternatively, the particles can be coated with a magnetic material, or they can be disposed within a magnetic solution. Exemplary magnetic materials include, by way of non-limiting example, iron compounds such as $Fe(OH)_2$ or compounds containing $Fe^{+2}$ or $Fe^{+3}$ ions. In use, the magnetic nanoparticles can be applied to tissue to be treated using various methods, including those previously discussed. The location of the particles can be identified using light, and once identified an alternating current can be delivered to the particles to induce inductive heating. As a result, the magnetic nanoparticles will generate heat, thereby cauterizing or otherwise treating the tissue. The use of magnetic particles in combination with fluorescent nanoparticles is particularly advantageous as the fluorescent nanoparticles enable precise identification of the tissue being treated, thereby limiting or avoiding damage to healthy tissue.

In another embodiment, a sensor can be provided for sensing the tissue temperature to enable a desired temperature range to be maintained during energy delivery. The sensor can be disposed on a distal end of a device, such as an endoscope, catheter, or other delivery device, and it can be coupled to an external apparatus that displays the measured temperature. In certain exemplary embodiments, the temperature of the tissue being treated is brought to a temperature above about 150° F. The magnetic particle property may also be used to steer the particle to a preferred location or to cause the particles to accumulate at a preferred location. For example, a magnet can be positioned in the vicinity of the particles, for example, adjacent to an external tissue surface, and the magnet can be manipulated to cause the particles to move in a desired direction.

Figure 3A:
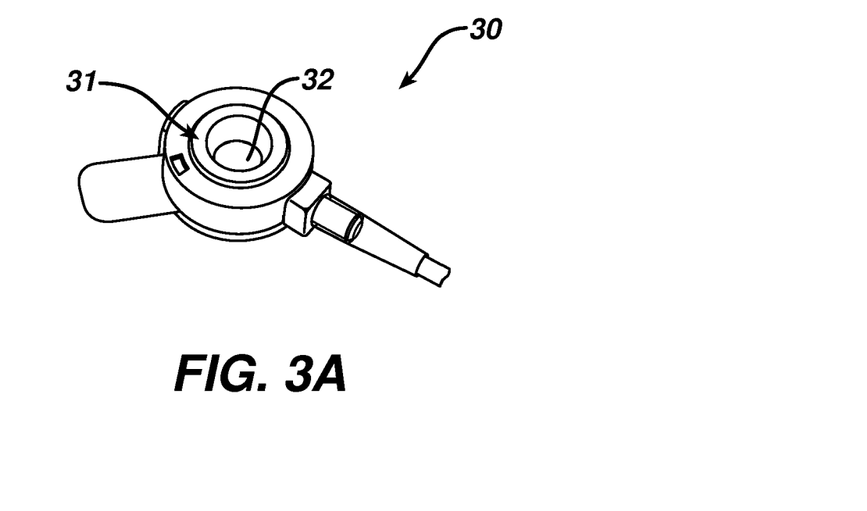
FIG. 3A is a top view of a drug delivery pump having fluorescent nanoparticles disposed around a bolus port for locating the bolus port once the pump is implanted.
Figure 3B:
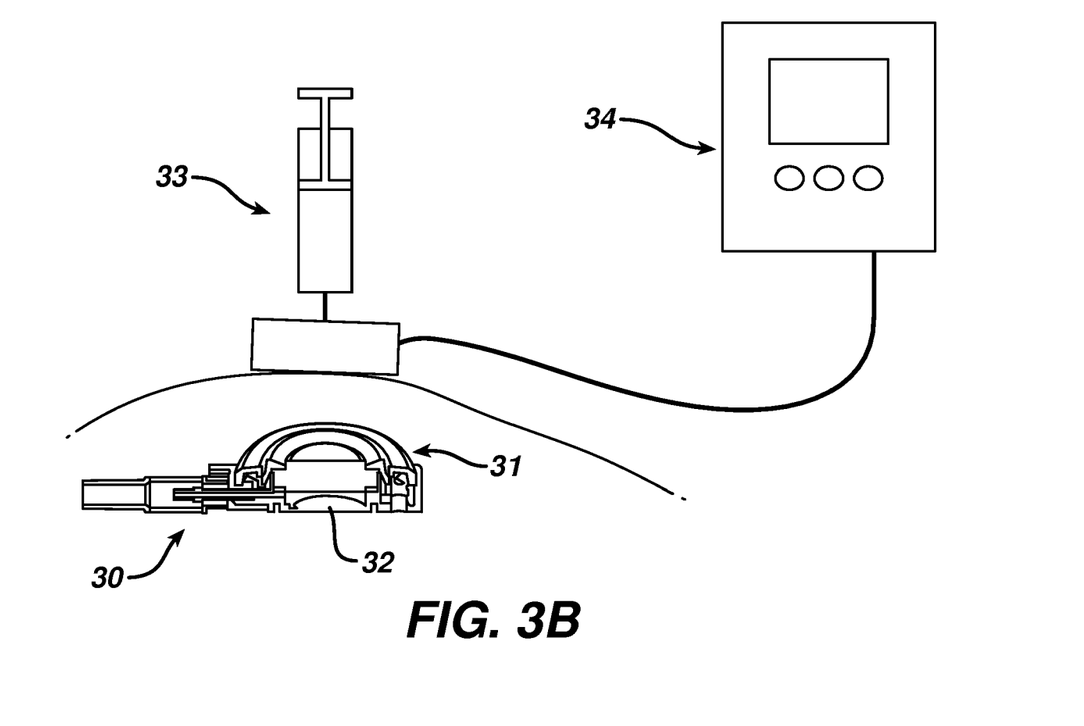
FIG. 3B is a side view of the drug delivery pump of FIG. 3A implanted in tissue, showing a reading unit with a fluorescence meter for identifying and locating the particles in the port and a syringe about to be inserted through the port.

In another embodiment, fluorescent nanoparticles can be used on medical devices to indicate the location and/or orientation of the device once introduced into a patient's body, or to illuminate a body cavity within which the device is disposed. For example, fluorescent nanoparticles can be coated onto, embedded within, or disposed within an implant to enable future location and identification of the implant. The particles, or a liquid or solid containing the particles, can also be disposed within a capsule or other structure, and that structure can in turn be disposed within an implant. By way of non-limiting example, the nanoparticles can be placed around a port, such as a bolus port in a drug pump or a fluid-refill port in a gastric band. FIG. 3A illustrates a drug delivery pump 30 having a bolus port 31 with nanoparticles 32 disposed therearound. The nanoparticles can be used to locate the port and allow easy access for introducing and removing fluids to and from the port. For example, FIG. 3B illustrates the nanoparticles radiating through the tissue to enable location of the port, thereby allowing a syringe 33, as shown, to be inserted into the port. A reading unit 34 with a fluorescence meter can be used to identify and locate the particles and thus the port.

Figure 4:
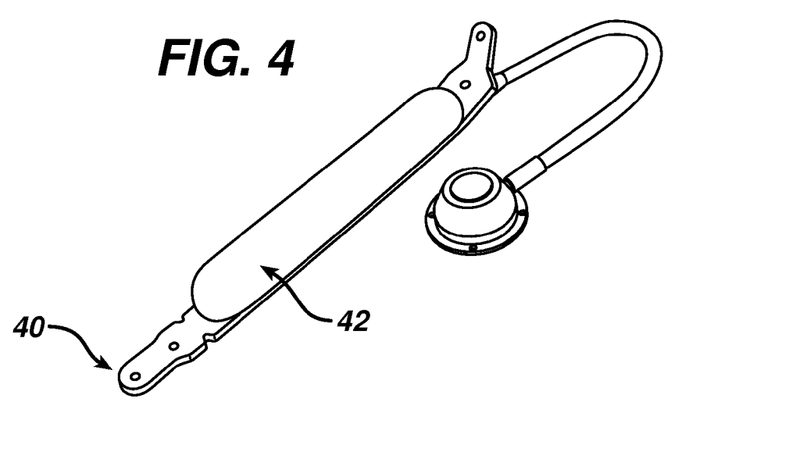
FIG. 4 is a perspective view of a gastric restriction band having fluorescent nanoparticles disposed thereon for indicating a size of the band.

The nanoparticles can also be used to indicate size and/or directional orientation. For example, the nanoparticles can be located around a gastric band, either by coating the particles onto the band, embedding the particles in the band during manufacturing, or filling the band with a nanoparticle-containing solution. FIG. 4 illustrates a gastric band 40 having a balloon disposed along the length thereof and containing nanoparticles or a nanoparticle solution 42. In use, the gastric band 40 is positioned around the stomach to decrease the size of the stomach. The nanoparticles in the band 40 can be viewed to determine the size or diameter of the gastric band 40, thereby enabling a surgeon to easily determine whether any adjustments are necessary. If the band 40 is too small or too large, fluid can be added to or removed from the band 40.

Figure 5A:
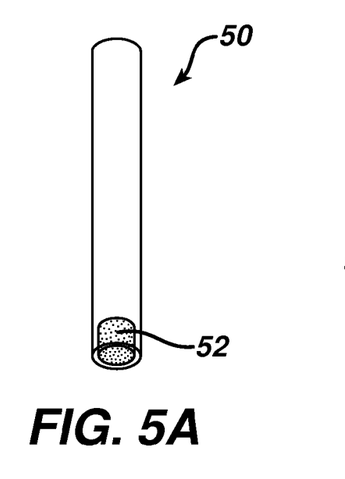
FIG. 5A is a side view of an elongate shaft having fluorescent nanoparticles disposed around a distal end thereof for illuminating a body cavity.
Figure 5B:
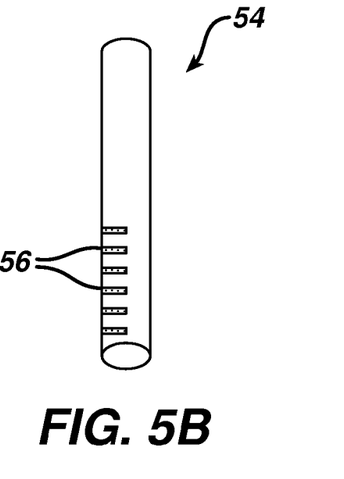
FIG. 5B is a side view of an elongate shaft having fluorescent nanoparticles disposed on a distal end thereof for indicating an insertion depth of the elongate shaft into a body lumen.
Figure 5C:
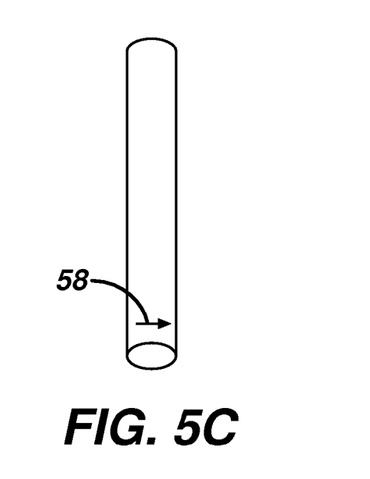
FIG. 5C is a side view of an elongate shaft having fluorescent nanoparticles disposed to form an arrow indicating a direction orientation of a distal end of the elongate shaft.

In yet another embodiment, a catheter, endoscope, or other devices that are introduced into body can have nanoparticles positioned to allow the location of a distal end of the device to be identified during use, to indicate a directional orientation of the device, and/or to illuminate an area surrounding a portion of the device. By way of non-limiting example, FIG. 5A illustrates an elongate shaft 50, such as a catheter or endoscope, having nanoparticles 52 disposed around a distal end thereof to illuminate tissue surrounding the distal end of the device 50. The use of nanoparticles for illumination is particularly advantageous as it eliminates the need for a separate light source on the device. The particles could also be positioned to form indicia that indicate a directional orientation or physical end of the device. For example, FIG. 5B illustrates an elongate shaft 54, such as a catheter or endoscope, having particles disposed on the device so as to form a series of parallel lines 56 along a length of the distal end of a device 54. The lines 56 can thus be used to indicate the insertion depth of the distal end of the device 54 into a body lumen or to provide a reference for use with anatomical features. The lines could also be in the form of a bar code containing data, such as the manufacturer, lot code, or date of manufacture, that can be obtained from the device without having to remove the device from the body. The nanoparticles could also be disposed to form one or more directional indicators, such as an arrow 58 as shown in FIG. 5C, that enables a surgeon to determine the particular directional orientation of the device within a body lumen or cavity. In yet another embodiment, the nanoparticles can be located or, disposed within, or embedded in an absorbable material, such as a suture or fastener, that would leave the nanoparticles in the tissue after the absorbable material is absorbed. A person skilled in the art will appreciate that various techniques can be used to position one or more nanoparticles on or in a device or implant.

Various exemplary methods and devices are also provided to excite the fluorescent nanoparticles to enable viewing. In an exemplary embodiment, electromagnetic energy can be delivered to fluorescent nanoparticles disposed within a patient's body using a delivery apparatus, such as an endoscope or laparoscope. The delivery apparatus can be located externally, e.g., above the tissue surface, or internally. The excitation source can include any device that can produce electromagnetic energy at wavelengths that correspond to the absorption cross-section of the nanoparticles, including but not limited to, incandescent sources, light emitting diodes, lasers, arc lamps, plasma sources, etc. Various imaging technologies can also be used for detecting, recording, measuring or imaging fluorescent nanoparticles. In an exemplary embodiment, the imaging technology is adapted to reject excitation light, detect fluorescent light, form an image of the location of the nanoparticles, and transmit that image to either a storage or display medium. Exemplary devices include, for example, a flow cytometer, a laser scanning cytometer, a fluorescence micro-plate reader, a fluorescence microscope, a confocal microscope, a bright-field microscope, a high content scanning system, fiber optic cameras, digital cameras, scanned beam imagers, analog cameras, telescopes, microscopes and like devices.

Figure 6:
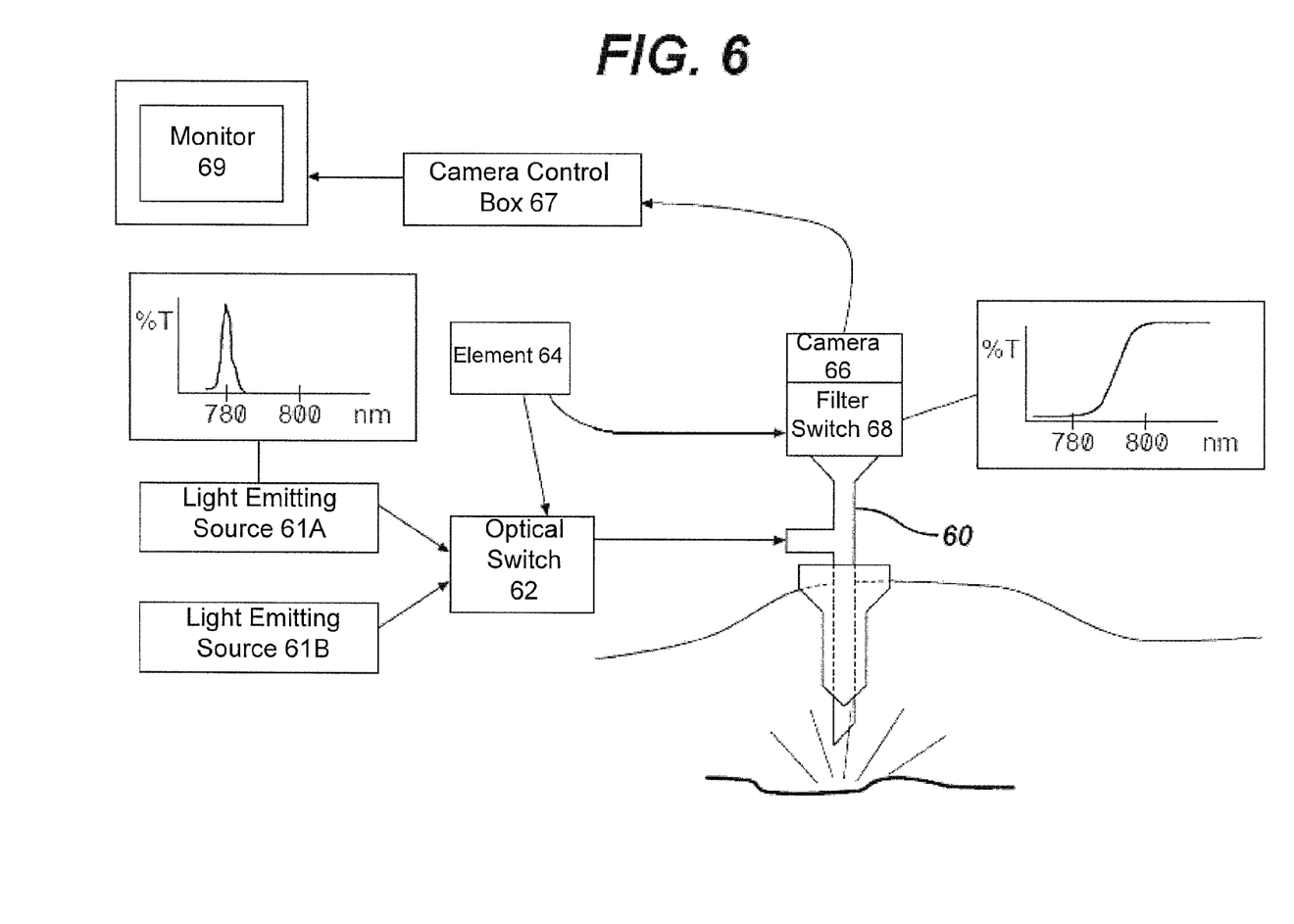
FIG. 6 is a diagram illustrating one embodiment of a laparoscopic system for viewing fluorescent nanoparticles.

In an exemplary embodiment, the energy source is light, i.e., electromagnetic radiation, and the reading apparatus has an elongate shaft that is adapted to be inserted into a body lumen and that includes a light emitting mechanism and an image receiving apparatus. Since fluorescent nanoparticles formed from a fluorophore core and a silica shell can absorb and emit energy in the visible, infrared, and near infrared frequencies, and they are illuminated at one wavelength and observed at a different shifted wavelength, it is desirable to provide an imaging apparatus that can enable visualization of such nanoparticles. FIG. 6 illustrates one exemplary embodiment of a laparoscope 60 that has two illumination or light emitting sources, generically illustrated as elements 61A, 61B. As shown, the laparoscope 60 utilizes an optical switch 62 to select the illumination source(s). One illumination source may be a standard white light source, such as a Xenon arc lamp used in standard endoscopic systems for illuminating and viewing in the visible spectrum. The second light source may be a narrow-band source associated with the absorbance cross-section of the nanoparticles, such as a laser, LED, mercury source, or filtered broadband source. One exemplary narrow-band source is a 780 nm pigtailed laser diode. The optical switch 62 can connect the selected source 61A, 61B to an optical fiber bundle (not shown) that extends through the laparoscope 60 for transmitting the light through an eyepiece at the distal end of the laparoscope 60. When the light is transmitted, e.g., by depressing a switch, button, or foot pedal, generically illustrated as element 64, the fluorescent nanoparticles N on the tissue will excite and fluoresce. The laparoscope 60 can also include an image receiving apparatus or camera 66 for collecting the reflected light from the fluorescent nanoparticles, and a filter switch 68 to place the appropriate optical filter between the eyepiece and the camera 66. The filter that is used for visualization of the nanoparticles N, for example, must be highly efficient at rejecting the excitation wavelength in order to avoid saturation of the camera 66, while still being highly transparent at the wavelength of the emission of the nanoparticles N. One exemplary filter is an interferometric long-pass filter with four orders of magnitude of rejection at the excitation wavelength and over 80% transmission at the peak of the fluorescent band. As further shown in FIG. 6, the captured image can be transmitted to a monitor 69 that is coupled to the camera 66 by a camera control box 67. The monitor 69 can be an on-board monitor or an external monitor, as shown, or other reading devices can be used such as a readout display, an audible device, a spectrometer, etc. A person skilled in the art will appreciate that, while a laparoscope 60 is shown, various other elongate shafts, such as catheters and endoscopes, can be used to transmit and receive light for viewing fluorescent nanoparticles. The embodiment described illustrates real time viewing. A person skilled in the art will also appreciate that image(s) can be captured and stored for overlay transmission, such as showing a peristaltic pulse as a continuous path.

Additional utilization can also be achieved in the non-visible ranges, as previously indicated, by combining a visible light source with a non-visible light source enabling the ability to turn the non-visible image on or off. The images may be viewed either side by side or simultaneously by overlapping the images. The visible light source can vary and can be an ambient room source, an LED, a laser, a thermal source, an arc source, a fluorescent source, a gas discharge, etc., or various combinations thereof. The light source can also be integrated into the instrument or it may be an independent source that couples to the instrument.

Figure 7A:
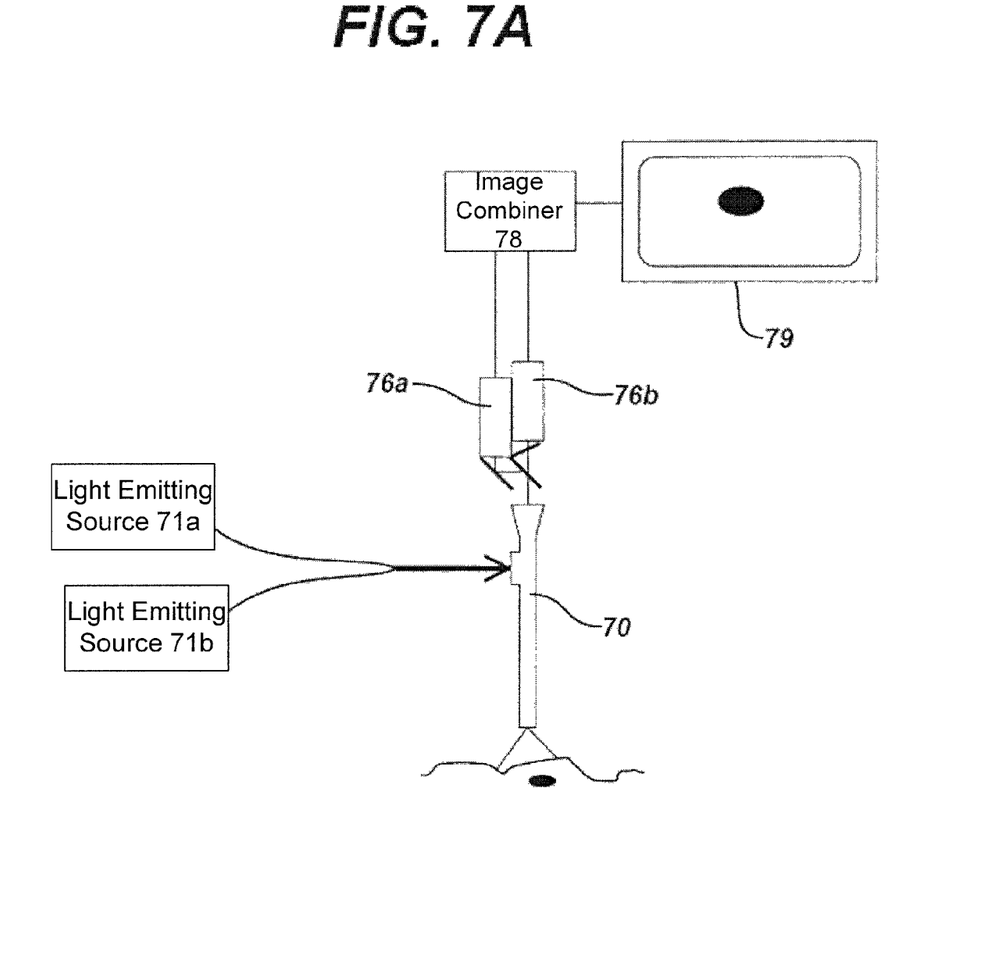
FIG. 7A is a diagram illustrating one embodiment of a laparoscope having an image combiner for viewing visible and non-visible wavelengths emitted by fluorescent nanoparticles.

FIG. 7A illustrates one embodiment of a laparoscope 70 that has the ability to overlay a fluorescent image onto a visible image to enable simultaneous viewing of both images. In this embodiment, both light sources, generically illustrated as 71a and 71b, can be combined into an illumination port of the laparoscope 70 using, for example, a bifurcated fiber (not shown). At the eyepiece of the scope 70 (located at the proximal end), a specialized optical fiber can be used to split the light to two separate cameras, generically illustrated as 76a and 76b. For example, a filter can reflect all visible light to a visible image camera 76a and can transmit all other light for receipt by the fluorescent camera 76b. A second interference filter can be placed in the transmitted path to direct only fluorescent waveband to the fluorescent camera 76b. Both camera outputs can be combined using an image combiner, generically illustrated as 78, and the images can be overlaid using techniques well known in the art to display, e.g., on a monitor 79, a simultaneous image. In an exemplary embodiment, the fluorescent image can be color-shifted to stand out relative to the visible display.

Figure 7B:
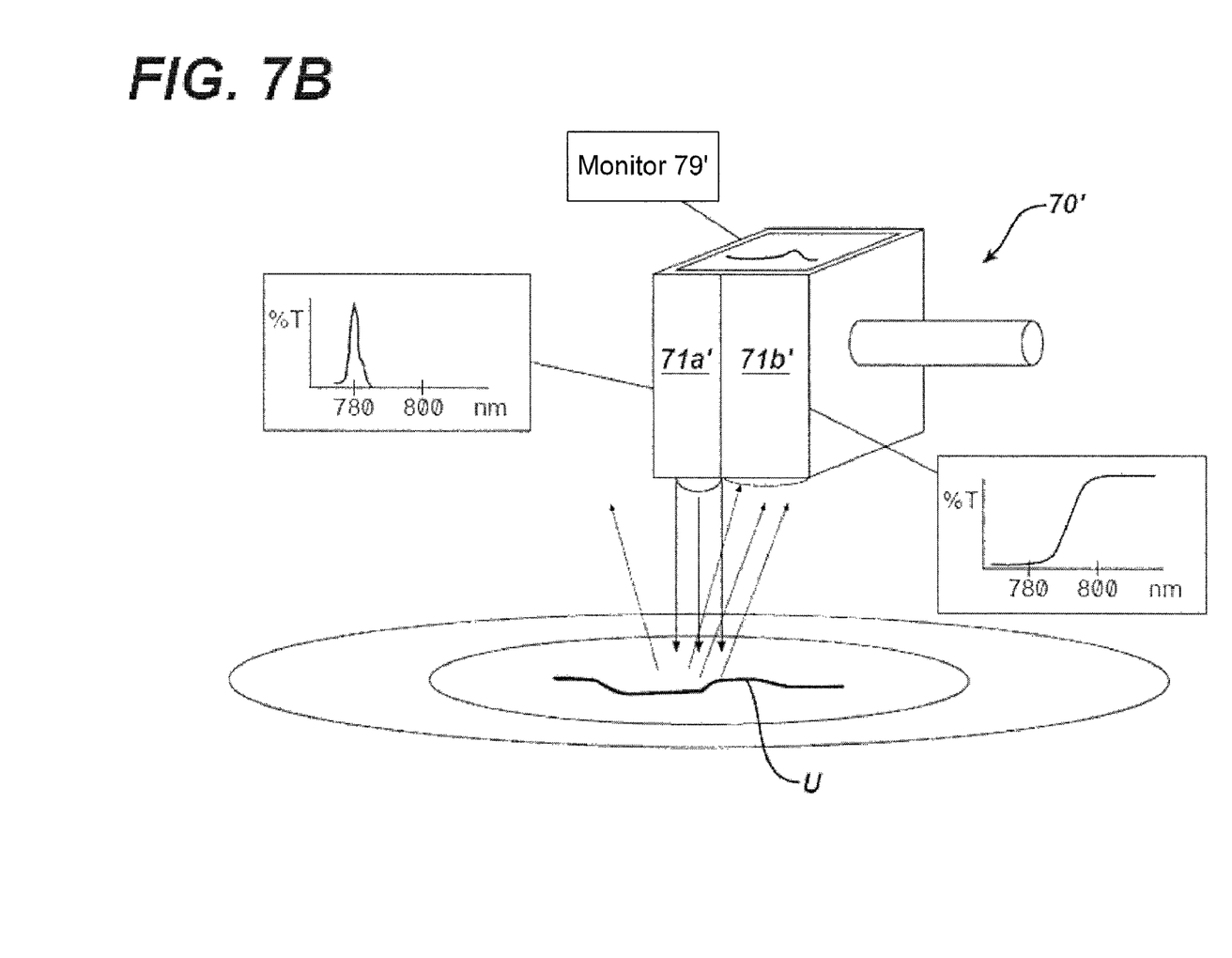
FIG. 7B is a diagram illustrating the embodiment of FIG. 7A incorporated into a hand held instrument with a self-contained monitor or display output that feeds to other displays.

FIG. 7B shows yet another embodiment where the above-described capability can be incorporated into a hand held instrument with a self-contained monitor or display output that can feed to other displays, such as those noted above. In particular, FIG. 7B illustrates a device 70' having two illumination or light emitting sources, generically illustrated as elements 71a', 71b', that are located within a housing having a monitor or display 79' located on the proximal-most end thereof The light sources 71a', 71b' can be similar to those previously described above with respect to FIG. 6, and the housing can also include other features, such as a filter switch, an optical switch, etc., as previously described above. In use, light can be delivered to tissue to cause the nanoparticles to fluoresce. As shown in FIG. 7B, an infrared excitation beam is delivered to a ureter U having several nanoparticles therein, and the image is viewed on the on-board display 79'.

Figure 8A:
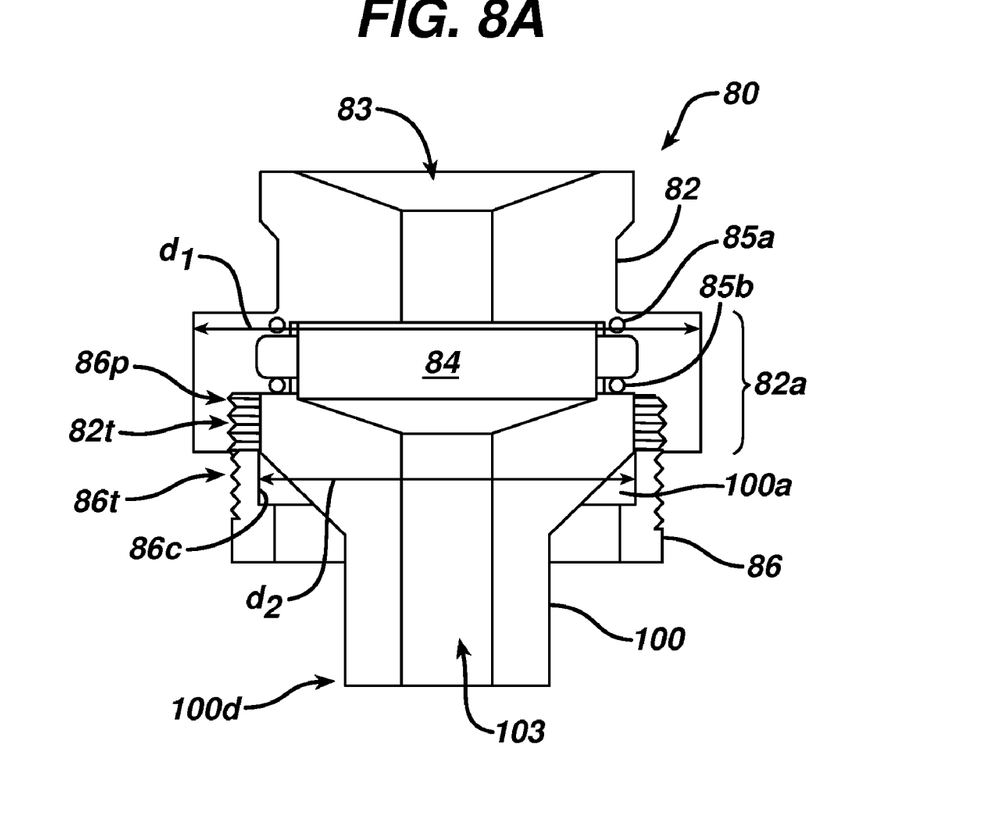
FIG. 8A is a cross-sectional view of one embodiment of an adaptor mated to an endoscope eyepiece.

FIG. 8A illustrates one exemplary embodiment of an adaptor 80 for enabling a conventional laparoscope or endoscope to view fluorescent nanoparticles. A person skilled in the art will appreciate that while an endoscope is shown, the adaptor can be used on any type of scope, including scopes used during open, endoscopic, and laparoscopic procedures. As shown, the adaptor 80 generally includes first and second members, e.g., an extension eyepiece 82 and a mating element 86, that are adapted to capture an endoscope eyepiece 100 therebetween. The adaptor 80 can also be configured to seat a filter 84 therein between the endoscope eyepiece 100 and the extension eyepiece 82. The extension eyepiece 82 can have a variety of configurations, but in an exemplary embodiment the extension eyepiece 82 is adapted to extend the eyepiece on the proximal end of a standard scope. As shown in FIG. 8A, the extension eyepiece 82 has a generally cylindrical shape with a viewing window or lumen 83 formed therethrough and adapted to be aligned with the viewing window or lumen 103 formed in the eyepiece 100 of a scope. The extension eyepiece 82 can also include an enlarged region 82a having a diameter $d_1$ greater than a diameter $d_2$ of the endoscope eyepiece 100 to allow the enlarged region 82a to be disposed around at least a portion of the endoscope eyepiece 100. As further shown, the extension eyepiece 82 can include a cavity formed therein for seating the filter 84, as shown. The illustrated cavity is formed in the enlarged diameter region, and it extends across the path of the lumen 83 such that the filter 84 will extend across and between the viewing path of the eyepieces 82, 100 to thereby filter light viewed through the eyepieces 82, 100. The filter 84 can be used to block out visible light, thereby enabling clear viewing of the non-visible wavelengths. As further shown, the adaptor 80 can also include a mating element 86 for mating the extension eyepiece 82 to the endoscope eyepiece 100. While various mating elements can be used, in the illustrated embodiment the mating element 86 is in the form of a ring having a lumen extending therethrough with an enlarged cavity 86c formed in a proximal end 86p thereof for receiving an enlarged diameter portion 100a formed on the proximal end of the eyepiece 100. The mating element 86 can be loaded onto the eyepiece 100 by removing the eyepiece 100 and sliding the mating element 86 over the distal end 100d of the eyepiece 100. As a result, the eyepiece 100 will be positioned between the mating element 86 and the extension eyepiece 82. The mating element 86 can also include threads 82t formed on an outer surface thereof for mating with threads 86t formed within a cavity in a distal end of the extension eyepiece 82. Thus, the mating element 86 can be disposed around the eyepiece 100 and threaded into the extension eyepiece 82 to engage the enlarged diameter portion of the endoscope eyepiece 100, as well as the filter 84, therebetween. The extension eyepiece 82 can also include one or more seals disposed therein to cushion the filter when the mating element 86 is threaded onto the extension eyepiece 82. FIG. 8A illustrates first and second seals 85a, 85b, such as o-rings, disposed within grooves formed in the extension eyepiece adjacent to superior and inferior surfaces of the filter 84. The seals 85a, 85b are positioned radially around the superior and inferior surfaces of the filter 84, and in use when the mating element 86 is threaded onto the extension eyepiece 82, the seals 85a, 85b will cushion the filter 84 as the scope eyepiece 100 abuts against the bottom seal 85b.

Figure 8B:
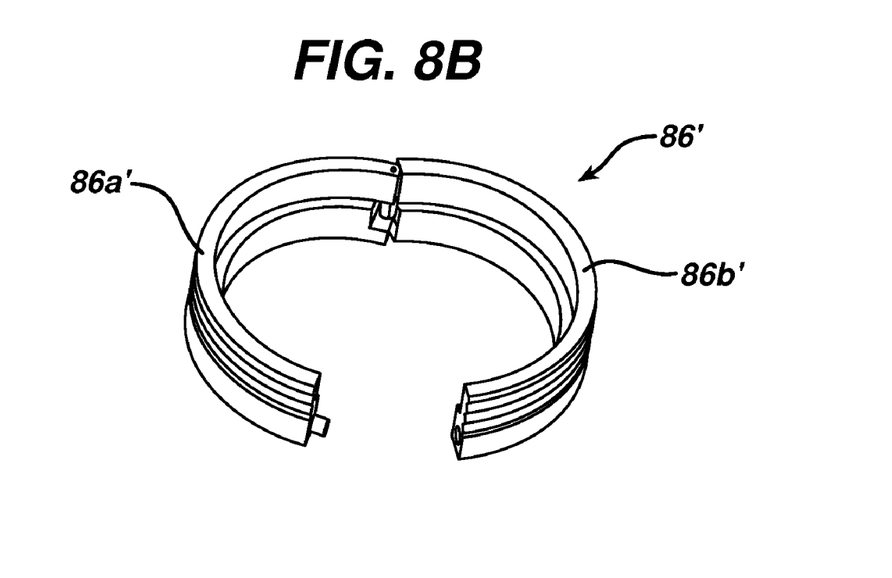
FIG. 8B is perspective view of one embodiment of mating element for use with an adaptor configured to mate to an endoscope eyepiece.

In other embodiments, where the eyepiece on the endoscope is not removable, the mating element can be formed from two halves that mate together to allow the mating element to be positioned around the eyepiece. FIG. 8B illustrates one embodiment of a mating element 86' having two halves 86a', 86b' that mate together. In the illustrated embodiment, the two halves 86a', 86b' are hingedly connected, however they can optionally be totally separable from one another. The mating element halves 86a', 86b' can also include other features to facilitate alignment of the halves with one another. For example, the two halves can include a pin and bore connection, as shown, for aligning the two halves. An alignment mechanism is preferred in order to align the threads on the two halves to enable threading of the mating element into the extension eyepiece. A person skilled in the art will appreciate that the mating element and the extension eyepiece can be mated using a variety of other mating techniques, such as a snap-fit connection, a luer lock, an interference fit, etc.

Figure 9:
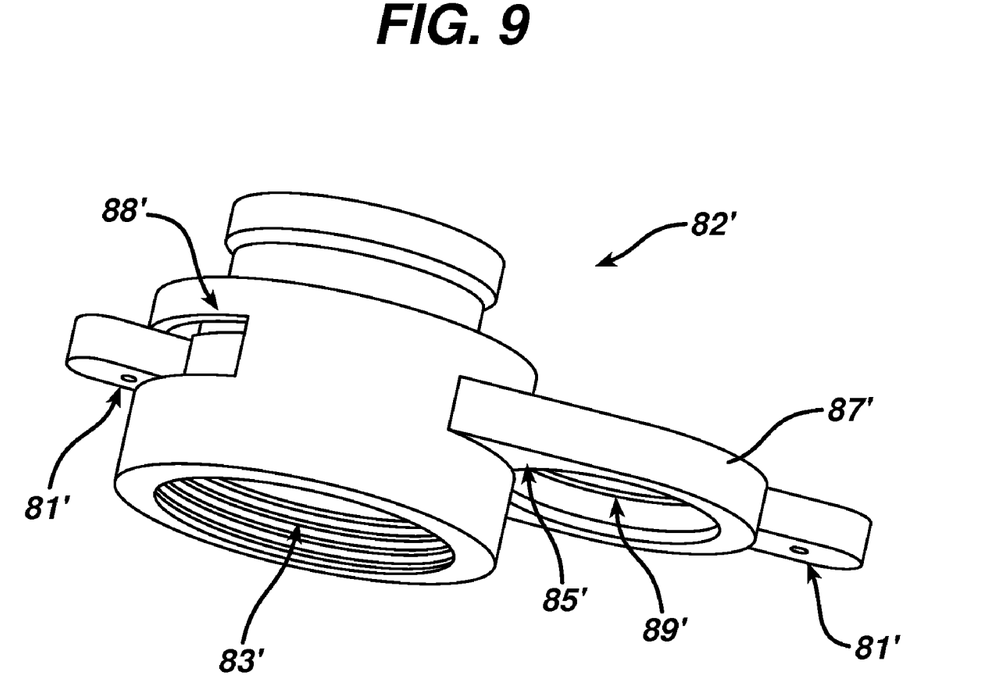
FIG. 9 is a perspective view of another embodiment of a portion of an adaptor for mating to an endoscope, showing a removable filter cartridge.

In another embodiment, the filter can be removable. FIG. 9 illustrates one such embodiment of an extension eyepiece 82' having a removable filter cartridge 87'. As shown, the extension eyepiece 82' includes a cut-out or slot 88' extending therethrough and across the viewing lumen 83'. The slot 88' is configured to slidably and removably receive a filter cartridge 87' such that a filter 89' held within the filter cartridge 87' is aligned with the viewing lumen 83' in the extension eyepiece 82' to thereby filter light passing therethrough. The filter cartridge 87' can thus be removed and replaced with another filter cartridge 87', or alternatively the filter 89' in the filter cartridge 87' can be replaced to enable different types of filters to be disposed within the extension eyepiece 82'. In an exemplary embodiment, as shown, the filter cartridge 87' includes two side-by-side slots for seating two filters (only one filter 89' is shown, the other filter is disposed within the eyepiece 82'). The filter cartridge 87' can also include a hole 81' formed in each end thereof for receiving a pin (not shown) that is configured to function as a stop to selectively align each filter with the viewing lumen as the filter cartridge 87' is slid back and forth.

As previously discussed with respect to FIG. 8A, the cartridge 87' can also include one or more seals disposed therein. In this embodiment, the seals are particularly effective for preventing incident light from entering into the viewing lumen through the slot 88'. The seals can also assist in aligning the filters with the eyepiece 82'. For example, as shown in FIG. 8B, the cartridge 87' can include a groove 85' formed therein around the filter 89'. While not shown, grooves can be formed on both the top and bottom surfaces of the cartridge 87', and around both filters such that the cartridge includes a total of four grooves. The cartridge 87' can also include one or more seals (not shown), such as o-rings, disposed therein. When the cartridge 87' is slid into the slot 88' in the eyepiece 82', the seals will extend into and engage the grooves extending around the filter, thereby aligning the filter with the viewing lumen in the extension eyepiece and also preventing incident light from entering the viewing lumen. A person skilled in the art will appreciate that a variety of other techniques can be used to provide an interchangeable filter. For example, a kit containing multiple adaptors, or multiple extension eyepieces, having different filters can be provided.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
    delivering at least one fluorescent nanoparticle to tissue, the at least one fluorescent nanoparticle comprising a fluorescent, non-metallic center core and a biocompatible, non-metallic shell surrounding the fluorescent, non-metallic center core;
    delivering visible light to the tissue to cause a first dye contained within the at least one fluorescent nanoparticle to emit visible light;
    locating the tissue using the visible light;
    after locating the tissue using the visible light, delivering invisible light to the tissue to cause a second dye contained within the at least one fluorescent nanoparticle to emit invisible light; and
    determining a precise location of the tissue using the invisible light.

2. The method of claim 1, wherein locating the tissue using the visible light comprises delivering visible light to at least one fluorescent nanoparticle located at or adjacent to a surface of the tissue, and determining a precise location of the tissue using the invisible light comprises delivering the invisible light to at least one fluorescent nanoparticle located deep within the tissue.

3. The method of claim 1, wherein the at least one fluorescent nanoparticle is delivered in a carrier solution.

4. The method of claim 1, wherein the at least one fluorescent nanoparticle is injected into the tissue.

5. The method of claim 1, wherein the at least one fluorescent nanoparticle is delivered into the tissue using an intravenous catheter.

6. The method of claim 1, wherein delivering at least one fluorescent nanoparticle to tissue comprises delivering at least one fluorescent nanoparticle into a kidney, and wherein the at least one fluorescent nanoparticle has a property such that the kidney filters the at least one fluorescent nanoparticle into the ureter.

7. The method of claim 1, wherein delivering at least one fluorescent nanoparticle to tissue comprises delivering at least one fluorescent nanoparticle into a liver, and wherein the at least one fluorescent nanoparticle has a property such that the liver filters the at least one fluorescent nanoparticle into the colon.

8. The method of claim 1, wherein the at least one fluorescent nanoparticle is applied to tissue to be removed.

9. The method of claim 8, further comprising locating the tissue using the visible light, and using the invisible light to remove the tissue containing the at least one fluorescent nanoparticle.

10. The method of claim 1, wherein the fluorescent core contains the first and second dyes.

11. The method of claim 1, wherein the at least one fluorescent nanoparticle has a fluorophore core surrounded by a silica shell, the fluorophore core containing the first and second dyes.

12. The method of claim 1, further comprising:
    receiving the emitted visible light at a first image receiving apparatus configured to collect the emitted visible light;
    receiving the emitted invisible light at a second image receiving apparatus configured to collect the emitted invisible light;
    displaying a first image of the emitted visible light received by the first image receiving apparatus, a second image of the emitted invisible light received by the second image receiving apparatus, or a third image including an overlay of the first and second images; and
    determining whether to display the first image, the second image, or the third image based on a user selection of which image to display.

13. The method of claim 1, wherein delivering the at least one fluorescent nanoparticle comprises delivering the at least one fluorescent nanoparticle to a ureter, the emitted visible light being used to locate the ureter, and the emitted invisible light being used to determine a precise location of a ureter path of the ureter.

* * * * *